United States Patent [19]

Kronenthal et al.

[11] 4,006,747
[45] Feb. 8, 1977

[54] SURGICAL METHOD

[75] Inventors: Richard L. Kronenthal, Fairlawn; Matthew H. Wykoff, Somerville, both of N.J.

[73] Assignee: Ethicon, Inc., Somerville, N.J.

[22] Filed: Apr. 23, 1975

[21] Appl. No.: 571,043

[52] U.S. Cl. .................................. 128/335; 128/337
[51] Int. Cl.² .......................................... A61B 17/04
[58] Field of Search ............ 128/334 R, 335, 335.5, 128/337, 339, 340; 24/150 R, 150 FP

[56] References Cited

UNITED STATES PATENTS

| | | | |
|---|---|---|---|
| 3,103,666 | 9/1963 | Bone | 227/67 |
| 3,209,422 | 10/1965 | Dritz | 24/150 R X |
| 3,513,848 | 5/1970 | Winston et al. | 128/335 |
| 3,527,223 | 9/1970 | Shein | 128/329 |
| 3,541,591 | 11/1970 | Hoegerman | 128/335 |
| 3,636,956 | 1/1972 | Schneider | 128/335.5 |
| 3,664,345 | 5/1972 | Dabbs et al. | 128/335 |
| 3,716,058 | 2/1973 | Tanner | 128/337 |

Primary Examiner—Dalton L. Truluck
Attorney, Agent, or Firm—Wayne R. Eberhardt

[57] ABSTRACT

A method for closing wounds and surgical incisions in mammalian tissue which comprises fastening an approximated wound or incision with a series of devices comprising a short filament with a head on each end, each device being surgically placed so that the filament traverses the wound or incision within the tissue while one head of the device engages the surface of the tissue on either side of the wound or incision. Apparatus is provided for the surgical placement of the device.

15 Claims, 9 Drawing Figures

U.S. Patent  Feb. 8, 1977  4,006,747
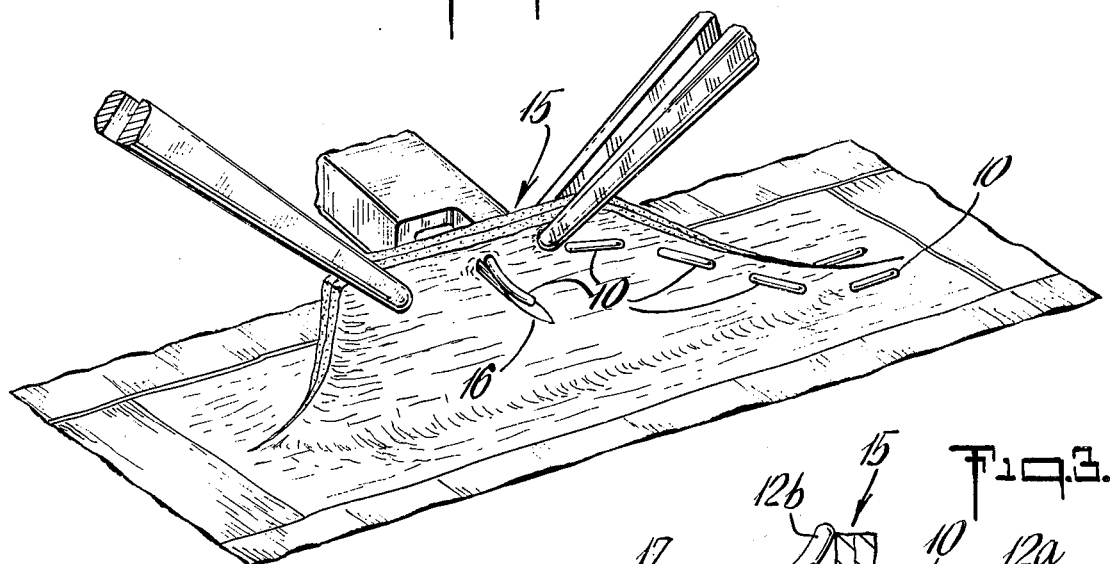
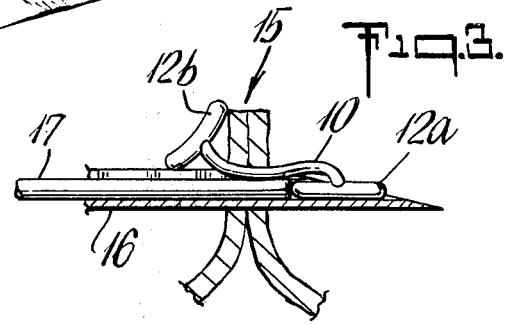
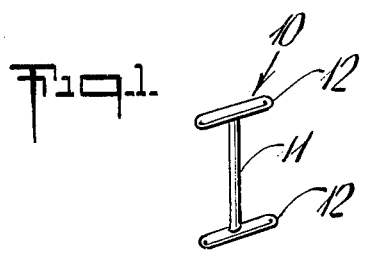
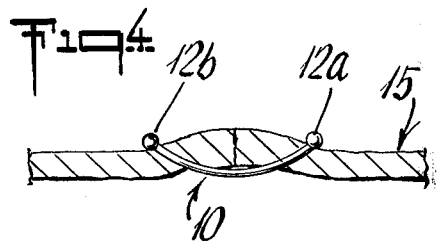
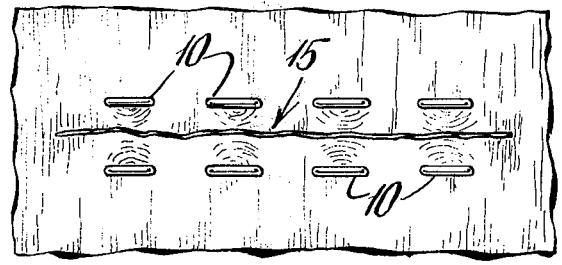
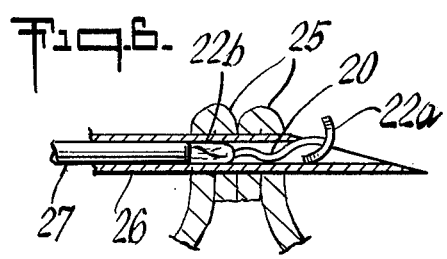
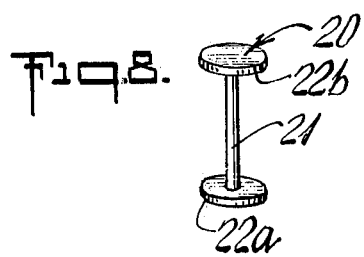
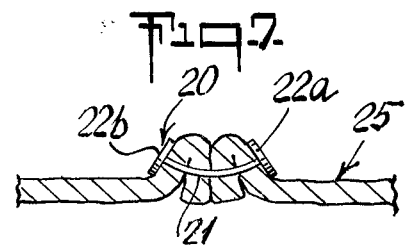

SURGICAL METHOD

BACKGROUND OF THE INVENTION

1. Field of Invention

This invention relates to the surgical closure of wounds or incisions to allow healing, and more particularly to a method for effecting such closure utilizing a series of individual wound closure devices.

2. Description of Prior Art

Wounds and surgical incisions are conventionally closed by the time honored technique of simply sewing the wound closed with needle and suture. Needle shapes and sizes and suture sizes and compositions have been developed over the years to meet the demands of many different suturing situations, from delicate anastomoses and ophthalmic work to the less demanding approximation of skin and fascia.

Because the procedure of sewing up a wound and tying sutures can be rather tedious and time consuming, the art of stapling was developed as an alternate to suturing in certain applications. The art is replete with devices and designs of staples and staple appliers for surgical use, and such devices have now been widely accepted by the medical profession.

The present invention has for an object providing a further alternative to suturing or stapling for wound closure which is fast, inexpensive and efficient. It is a further object of this invention to provide a new method for closing mammalian tissue, particularly skin, muscle and fascia. It is a yet further object of this invention to provide a method for closing surgical incisions in the skin which, when applied to animals, has less tendency to be clawed or bitten out by the animal. Still other objects of this invention will be apparent from the ensuing description and claims.

SUMMARY

Wounds and surgical incisions in mammalian tissue are closed and fastened for healing by placing a fastening device through and across the wound opening. The fastening devices comprise a short filament of a length sufficient to span the wound, with a restraining head on either end of the filament. The fastening device is passed through the tissue to be fastened by means of a hollow slotted needle adapted to receive one head of the fastener within the needle with the attached filament extending therefrom through the slot. The needle carrying one end of the fastener is passed through and across the wound and, upon exiting the tissue on the side of the wound opposite the point of entry, the head of the fastener is disengaged from the needle, whereupon the needle is withdrawn leaving the fastener in place.

The fasteners are conveniently H-shaped devices constructed of a flexible and resilient biocompatible material which may be either absorbable or non-absorbable in body tissue. A series of fasteners placed in close proximity along the length of the wound and would effectively close the wound and enable natural healing to proceed. Non-absorbable fasteners are removed from skin closures by snipping off one head and withdrawing the fastener with the opposite head.

DESCRIPTION OF DRAWINGS

FIG. 1 is a front view of a typical surgical fastener of this invention.

FIG. 2 is a view in perspective of the fasteners of FIG. 1 being used to close skin in a surgical procedure.

FIG. 3 is a view in cross section of a fastener being placed across the wound as in FIG. 2.

FIG. 4 is a side view in cross section of the fastener of FIG. 2 in place across a wound.

FIG. 5 shows a wound closed with a series of fasteners.

FIG. 6 is another view in cross section of a fastener being placed across the wound in a Lembert-type closure.

FIG. 7 is a side view in cross-section of the fastener of FIG. 5 in place across the wound.

FIG. 8 is a view in perspective of one type of fastener.

FIG. 9 is a view in perspective of another type of fastener.

DESCRIPTION OF PREFERRED EMBODIMENTS

The present invention relates to a method for closing wounds or incisions in mammalian tissue with a series of individual fastener devices. Each fastener device comprises a filament member of sufficient length to span the approximated wound from a point on either side of the wound, and anchoring means on each end of the filament to prevent the filament from pulling through the tissue. The method of the invention is particularly useful for closing skin, muscle (both smooth and skeletal) and fascia.

In a preferred embodiment, a hollow needle is utilized to insert the fastener through the tissue and across the wound. The tissue is approximated at the wound and the hollow needle is passed into the tissue from a point on one side of the wound and on through the tissue until the tip of the needle exits the tissue on the opposite side of the wound. The path of the needle is not unlike that used in conventional suturing. While in closing a wound by suturing, the needle and a length of attached suture are passed completely through the tissue, the hollow needle in the present case is inserted only far enough to penetrate through the tissue to form an open communication with both sides of the wound. The anchoring means on one end of the fastener device is then passed through the hollow needle until it is discharged from the tip of the needle on the far side of the wound. The needle is then withdrawn from the tissue while the fastener is restrained in the tissue by the anchoring means on the far side of the wound, until the needle is completely disengaged from the fastener and the tissue. The fastener is thus left in the tissue with the filament of the fastener traversing the wound along the path created by the needle and with the anchoring means engaging and restraining the surface of the tissue on either side of the wound.

The method and application of the present invention will be more fully understood and appreciated by reference to the ensuing description and drawings. FIG. 1 illustrates a preferred fastener design wherein filament member 11 is terminated at each end by rod shaped heads attached to the filament member at a point substantially equidistant from the ends of the rod member. FIG. 2 is a view in perspective of the fasteners of FIG. 1 being used to close the skin in a surgical procedure. The skin is approximated and raised by grasping with forceps and held while fasteners 10 are inserted in a row through both layers of skin 15 by means of hollow needle 16. Referring further to FIG. 3, fasteners 10 are individually inserted through the approximated tissue 15 via a slotted hollow needle 16 equipped with a push-rod 17. Head 12a of fastener 10 is contained within the needle with filament 11 extending therefrom through the slot of the needle. After the needle has passed completely through the tissue 15 and extends from the tissue on both sides of the wound, fastener head 12a is pushed out of needle 16 by push-rod 17 and needle 16 is withdrawn from the tissue leaving the fastener in place as shown in FIG. 4. The process is repeated until a series of fasteners have been placed through and across the wound as shown in FIG. 5. The fasteners are conveniently spaced as required to effect complete and continuous closure of the wound, with the heads 12 of adjacent fasteners in close proximity and in a uniform line along the entire length of the wound.

The present invention is not limited to any particular fastener design or method of placement, but includes the broad method of wound closure wherein the approximated wound is held in position for healing by a series of individual filaments which pass through and across the approximated wound and hold the tissue in a closed position by means of anchoring means at each end of the filament.

One alternative fastener design is illustrated in FIG. 8 wherein filament 21 is terminated at each end by flat disks 22. This type fastener is adapted to be completely contained within a hollow needle for placement across the wound as illustrated in FIG. 6 where fastener 20 is contained within needle 26 equipped with push-rod 27. Since the fastener is completely contained within the needle, needle 26 need not be slotted as described above for needle 16. After needle 26 is passed through tissue 25 on both sides of the wound, fastener 20 is pushed through the needle until head 22a exits the end of the needle. Needle 26 is then withdrawn from the tissue while fastener 20 is held stationary relative to the tissue by push-rod 27 until the needle is completely withdrawn leaving the fastener in place as shown in FIG. 7.

The fasteners and needle devices which may be used in the practice of the present invention are known in the art where they have been used for non-surgical applications such as attaching buttons or tags to fabrics or mending torn fabric. Fasteners such as that of FIG. 1 and slotted hollow needle devices for use therewith are disclosed in U.S. Pat. No. 3,470,834, 3,103,666, 2,069,878, 3,494,004, 3,399,432, 3,518,729 and Des. 213,418, all of which are incorporated herein by reference. Fasteners such as that of FIG. 8 and hollow needle devices for use therewith are disclosed in U.S. Pat. No. 3,209,422 which is also incorporated herein by reference.

In the practice of the surgical method of the present invention, it is of course preferably that the fasteners and the needle device be sterilized before use. This is readily accomplished using conventional techniques of ethylene oxide, radiation, or heat sterilization. Sterile devices and fasteners may be packaged in sealed containers to preserve sterility until ready for use. The practice of the present invention in surgical procedures is illustrated by the following examples where the fasteners and needle devices were sterilized with ethylene oxide prior to use.

EXAMPLE 1

A beagle dog was subjected to a laparotomy. The incision was approximately 10 cm long. The muscle and peritoneal layers were closed as one layer using eight H-shaped fasteners with a 10 mm filament and 6 mm heads placed at approximately 12 mm intervals along the total length of the wound. The skin was closed in a similar manner with the same type fasteners. The wound healed uneventfully. The external skin fasteners were removed after 7 days and the incision continued to heal with minimal scarring. It was noted that none of the fasteners had been removed by the animal as is commonly experienced with the use of sutures for skin closure.

EXAMPLE 2

A female beagle dog was subjected to a cystotomy. The bladder mucosa was approximated with 5/0 chromic catgut. The incision in the muscle which was 2 cm long was closed with four fasteners similar to those in FIG. 1 having a filament 2 mm long attached to a 6 mm rod at one end and an enlarged oval knob at the other. The fasteners were placed in approximately 6 mm intervals in a manner analogous to an interrupted Lembert inverting stitch. A 4 cm incision in the abdominal wall and skin were each closed with four H-shaped fasteners as described in Example 1. The wound healed uneventfully and the external fasteners were removed after 7 days. It was noted that none of the fasteners had been removed by the animal.

After 6 weeks, the animal was sacrificed and a necropsy examination conducted. There were no adhesions on the peritoneal surface of the bladder and no dehiscence of the abdominal wall or visceral adhesions to the incision line. Encapsulation of the internal fasteners was minimal. Healing throughout was very satisfactory.

The fasteners may be constructed of any of a wide variety of materials or combinations of materials. The filament portion of the fastener which traverses the wound is preferably flexible and biologically inert to avoid unfavorable tissue reaction. The heads of the fastener are conveniently molded from the same material as the connecting filaments although different compositions can be used if desired. Materials such as nylon and polypropylene which have found wide use as suture materials can be used to mold non-absorbable fasteners with good results. Other synthetic suture materials such as polyethylene terephthalate and homopolymers and copolymers of glycolide and lactide can also be used with good results. The glycolide and lactide polymers have the additional advantage of being absorbable in tissue and thus are particularly well suited for internal use in application where long-term maintenance of wound support is not required.

Where the heads of the fastener are to be of a composition different than that of the connecting filament, the filament is most conveniently fabricated from a length of suture material which may be monofilament or multifilament and natural or synthetic. Synthetic monofilaments include polyolefins and nylon, while natural monofilaments include catgut and collagen. Synthetic multifilaments include braided, twisted, and covered sutures of nylon, polyethylene terephthalate, and homopolymers and copolymers of glycolide and lactide. Natural multifilament sutures include braided, twisted, or covered silk, cotton and linen. Fastener heads may be attached to short lengths of the suture material by cementing, crimping, fusing, molding, or any other suitable method whereby the filament may be securely attached. One such embodiment of a composite fastener is illustrated in FIG. 9 wherein stainless steel heads 23a and 23b are each attached by swaging to multifilament suture 24 which enters the fastener head at the midpoint thereof with one end of the suture filament contained within one-half section of each head.

The examples described herein are for purposes of illustration only and the invention is not limited thereby. Many other variations in fastener construction and implantation devices will be apparent to those skilled in the art. For example, while the closure of wounds or incisions with the fastener devices described herein is most conveniently and preferably practiced with the use of a hollow needle as described, the hollow needle is not essential to the practice of this invention. For example, the fasteners may be positioned across the wound by inserting the fastener directly through a preformed hole, or by sharpening one end of a rod-shaped fastener head to serve as a needle and facilitate penetration of the tissue by that end of the fastener. These and other variations of the method disclosed and illustrated herein are accordingly included within the scope of the present invention.

What is claimed is:

1. A method of closing a wound or incision in mammalian tissue to facilitate the healing thereof which comprises (a) approximating the tissue at the wound; (b) inserting a hollow needle through the approximated tissue and across the wound whereby the needle is in communication with the surface of the tissue on either side of the wound; (c) passing one end of a fastener device comprising a filament member terminated at each end by first and second anchoring means through the hollow needle until said first anchoring means at one end of the fastener device is discharged from the end of said needle external of said tissue on one side of said wound; and (d) withdrawing the hollow needle from the tissue while maintaining the fastener device substantially stationary relative to the tissue until said fastener device is disengaged from the needle with said second anchoring means external of said tissue on the other side of said wound, whereby the fastener device remains in the tissue with the filament member traversing the wound through the tissue and with said first and second anchoring means maintaining the tissue in approximation at the wound from points on the surface of the tissue on either side of the wound.

2. A method of claim 1 wherein said anchoring means comprise rod members, each rod member being attached to said filament member at a point substantially equidistant from the ends of said rod member.

3. A method of claim 1 wherein said anchoring means comprise disk members, each disk member being attached to said filament member at a point substantially at the center of said disk.

4. A method of claim 1 wherein the fastener device is at least partially contained within the hollow needle while being inserted through the tissue.

5. A method of claim 2 wherein said hollow needle has a slot therein and one rod member of said fastener device is contained within said needle with the filament member extending from said needle through said slot while said fastener device is being inserted through the tissue.

6. A method of claim 1 wherein said fastener device is wholly contained within said hollow needle while being inserted through the tissue.

7. A method of claim 1 wherein a plurality of fastener devices are inserted through the tissue and across the wound along substantially the entire length of the wound.

8. A method of claim 1 wherein said fastener device is comprised of a non-absorbable material.

9. A method of claim 8 wherein the fastener device is comprised of nylon, polyolefin, or polyester.

10. A method of claim 8 wherein the filament member of said fastener device is comprised of a flexible, non-absorbable material and at least one of said anchoring means is comprised of a rigid, non-absorbable material.

11. A method of claim 10 wherein at least one of said anchoring means is stainless steel.

12. A method of claim 10 wherein said filament member is comprised of a multifilament suture material.

13. A method of claim 1 wherein said fastener device is comprised of a biologically absorbable material.

14. A method of claim 13 wherein said biologically absorbable material is selected from the group consisting of catgut, collagen, and homopolymers and copolymers of glycolide and lactide.

15. A method of claim 1 wherein the filament member of said fastener device is comprised of a biologically absorbable material and at least one of said anchoring means is comprised of a non-absorbable material.

* * * * *